United States Patent
Yuzawa

(10) Patent No.: US 12,406,376 B2
(45) Date of Patent: Sep. 2, 2025

(54) CONTOUR EXTRACTION DEVICE, CONTOUR EXTRACTION METHOD, AND CONTOUR EXTRACTION PROGRAM

(71) Applicant: FUJIFILM Corporation, Tokyo (JP)

(72) Inventor: Takuya Yuzawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 518 days.

(21) Appl. No.: 17/827,798

(22) Filed: May 30, 2022

(65) Prior Publication Data

US 2022/0292687 A1    Sep. 15, 2022

Related U.S. Application Data

(63) Continuation of application No. PCT/JP2020/040129, filed on Oct. 26, 2020.

(30) Foreign Application Priority Data

Dec. 16, 2019   (JP) .................. 2019-226791

(51) Int. Cl.
   *G06T 7/12*   (2017.01)
   *G06T 7/149*   (2017.01)
   *G06T 7/174*   (2017.01)

(52) U.S. Cl.
   CPC ............ *G06T 7/12* (2017.01); *G06T 7/149* (2017.01); *G06T 7/174* (2017.01); *G06T 2207/10081* (2013.01); *G06T 2207/30004* (2013.01)

(58) Field of Classification Search
   CPC ........... G06T 7/12; G06T 7/149; G06T 7/174; G06T 2207/10081; G06T 2207/30004;
   (Continued)

(56) References Cited

U.S. PATENT DOCUMENTS

| 7,110,583 | B2 | 9/2006 | Yamauchi |
| 10,453,199 | B2 | 10/2019 | Weistrand |

(Continued)

FOREIGN PATENT DOCUMENTS

| JP | H07249115 | 9/1995 |
| JP | 2002224116 | 8/2002 |

(Continued)

OTHER PUBLICATIONS

A. Goshtasby, D. A. Turner and L. V. Ackerman, "Matching of tomographic slices for interpolation," in IEEE Transactions on Medical Imaging, vol. 11, No. 4, pp. 507-516, Dec. 1992, doi: 10.1109/42.192686 (Year: 1992).*

(Continued)

Primary Examiner — Nay A Maung
Assistant Examiner — Dustin Bilodeau
(74) Attorney, Agent, or Firm — JCIPRNET

(57) ABSTRACT

A contour extraction device propagates a contour of a region of interest of a first tomographic image in a direction from the first tomographic image to a second tomographic image to extract first contours of the regions of interest of tomographic images between the first tomographic image and the second tomographic image, and propagates a contour of the region of interest of the second tomographic image in a direction from the second tomographic image to the first tomographic image to extract second contours of the regions of interest of tomographic images between the first tomographic image and the second tomographic image, and outputs a correction instruction for a contour in a third tomographic image between the first tomographic image and the second tomographic image in a case where a difference between the first contours and the second contours in the third tomographic image is a threshold value or more.

7 Claims, 5 Drawing Sheets

(58) Field of Classification Search
CPC . G06T 2207/10072; G06T 2207/20116; G06T 7/00; A61B 6/03
See application file for complete search history.

(56) References Cited

U.S. PATENT DOCUMENTS

| | | | |
|---|---|---|---|
| 2015/0078640 A1* | 3/2015 | Guo | G06T 7/12 |
| | | | 382/131 |
| 2016/0140726 A1 | 5/2016 | Jo et al. | |
| 2016/0278726 A1* | 9/2016 | Yamakawa | A61B 6/502 |
| 2018/0308291 A1 | 10/2018 | Waschbusch et al. | |
| 2019/0197692 A1* | 6/2019 | Weistrand | G06T 7/174 |

FOREIGN PATENT DOCUMENTS

| | | |
|---|---|---|
| JP | 2005224460 | 8/2005 |
| JP | 2005245734 | 9/2005 |
| JP | 2008259677 | 10/2008 |
| JP | 2013039246 | 2/2013 |
| JP | 2019535336 | 12/2019 |

OTHER PUBLICATIONS

"International Search Report (Form PCT/ISA/210) of PCT/JP2020/040129," mailed on Jan. 12, 2021, with English translation thereof, pp. 1-7.

"Written Opinion of the International Searching Authority (Form PCT/ISA/237)" of PCT/JP2020/040129, mailed on Jan. 12, 2021, with English translation thereof, pp. 1-6.

* cited by examiner

CONTOUR EXTRACTION DEVICE, CONTOUR EXTRACTION METHOD, AND CONTOUR EXTRACTION PROGRAM

CROSS-REFERENCE TO RELATED APPLICATIONS

This application is a Continuation of PCT International Application No. PCT/JP2020/040129 filed on Oct. 26, 2020, which claims priority under 35 U.S.C § 119(a) to Japanese Patent Application No. 2019-226791 filed on Dec. 16, 2019. Each of the above application(s) is hereby expressly incorporated by reference, in its entirety, into the present application.

BACKGROUND OF THE INVENTION

1. Field of the Invention

The present disclosure relates to a non-transitory computer readable recording medium storing a contour extraction device, a contour extraction method, and a contour extraction program.

2. Description of the Related Art

An ultrasonic diagnostic apparatus that extracts a contour of an object in a tomographic image by performing predetermined certain processing on the tomographic image is disclosed (see JP2002-224116A). This ultrasonic diagnostic apparatus performs interpolation processing using two contours extracted from tomographic images having two different time points in the past to extract a contour temporally positioned between the two contours from the tomographic image.

SUMMARY OF THE INVENTION

In the technique disclosed in JP2002-224116A, the contour may not always be extracted accurately because the ultrasonic diagnostic apparatus performs interpolation processing to extract the contour temporally positioned between the two contours from the tomographic image.

The present disclosure has been made in view of the above circumstances, and provides a contour extraction device, a contour extraction method, and a non-transitory computer readable recording medium storing a contour extraction program capable of accurately extracting a contour of a region of interest from a tomographic image.

There is provided a contour extraction device of the present disclosure comprising: at least one processor, in which the processor propagates a contour of a region of interest of a first tomographic image in a three-dimensional image, which is formed of a plurality of tomographic images, each including the region of interest, in a direction from the first tomographic image to a second tomographic image to extract first contours of the regions of interest of tomographic images between the first tomographic image and the second tomographic image, and propagates a contour of the region of interest of the second tomographic image in a direction from the second tomographic image to the first tomographic image to extract second contours of the regions of interest of tomographic images between the first tomographic image and the second tomographic image, and outputs a correction instruction for a contour in a third tomographic image between the first tomographic image and the second tomographic image in a case where a difference between the first contours and the second contours in the third tomographic image is a threshold value or more.

In the contour extraction device of the present disclosure, the processor may output the extracted contour of each tomographic image in a case where the difference is less than the threshold value.

Further, in the contour extraction device of the present disclosure, the processor, in a case where the difference is the threshold value or more, may extract the first contours and the second contours using a contour corrected in accordance with the correction instruction as the contour of the region of interest of the second tomographic image, in a tomographic image group from the first tomographic image to the third tomographic image, and may extract the first contours and the second contours using the contour corrected in accordance with the correction instruction as the contour of the region of interest of the first tomographic image, in a tomographic image group from the third tomographic image to the second tomographic image.

Further, in the contour extraction device of the present disclosure, the third tomographic image may be a middle tomographic image between the first tomographic image and the second tomographic image in the plurality of tomographic images.

Further, in the contour extraction device of the present disclosure, the processor may extract the first contours and the second contours using an active contour method.

Further, there is provided a contour extraction method of the present disclosure that is executed by a processor provided in a contour extraction device, the method comprising: propagating a contour of a region of interest of a first tomographic image in a three-dimensional image, which is formed of a plurality of tomographic images, each including the region of interest, in a direction from the first tomographic image to a second tomographic image to extract first contours of the regions of interest of tomographic images between the first tomographic image and the second tomographic image, and propagating a contour of the region of interest of the second tomographic image in a direction from the second tomographic image to the first tomographic image to extract second contours of the regions of interest of tomographic images between the first tomographic image and the second tomographic image; and outputting a correction instruction for a contour in a third tomographic image between the first tomographic image and the second tomographic image in a case where a difference between the first contours and the second contours in the third tomographic image is a threshold value or more.

Further, there is provided a non-transitory computer readable recording medium storing a contour extraction program of the present disclosure for causing a processor provided in a contour extraction device to execute a process comprising: propagating a contour of a region of interest of a first tomographic image in a three-dimensional image, which is formed of a plurality of tomographic images, each including the region of interest, in a direction from the first tomographic image to a second tomographic image to extract first contours of the regions of interest of tomographic images between the first tomographic image and the second tomographic image, and propagating a contour of the region of interest of the second tomographic image in a direction from the second tomographic image to the first tomographic image to extract second contours of the regions of interest of tomographic images between the first tomographic image and the second tomographic image; and outputting a correction instruction for a contour in a third tomographic image between the first tomographic image and the second tomographic image in a case where a difference between the first contours and the second contours in the third tomographic image is a threshold value or more.

According to the present disclosure, it is possible to accurately extract a contour of a region of interest from a tomographic image.

DESCRIPTION OF THE PREFERRED EMBODIMENTS

Hereinafter, an exemplary embodiment of the technique of the present disclosure will be described in detail with reference to the drawings.

Figure 1:
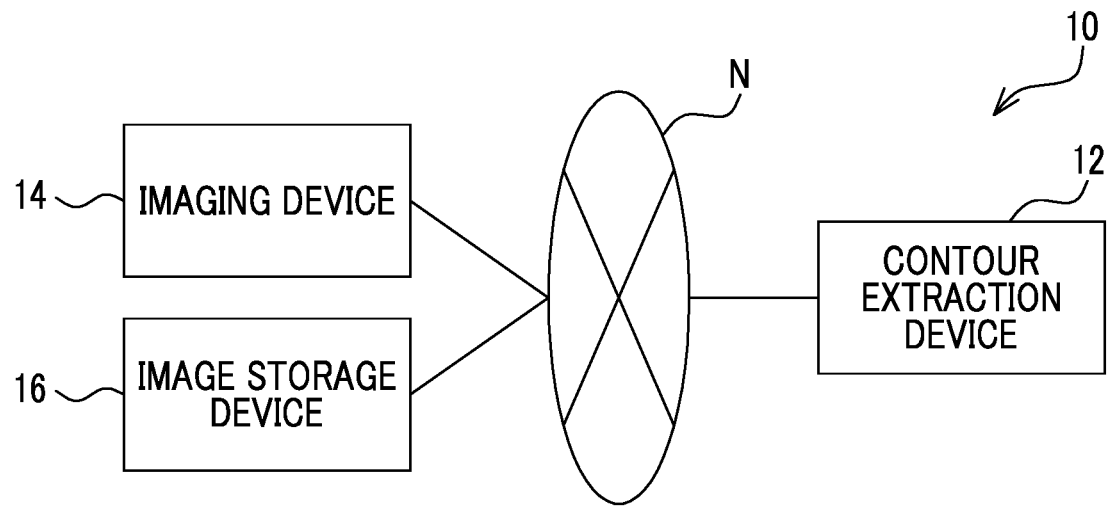
FIG. 1 is a block diagram showing an example of a configuration of a diagnosis support system.

First, the configuration of a diagnosis support system 10 according to the present embodiment will be described with reference to FIG. 1. As shown in FIG. 1, the diagnosis support system 10 includes a contour extraction device 12, an imaging device 14, and an image storage device 16. The contour extraction device 12, the imaging device 14, and the image storage device 16 are each connected to a network N and can communicate with each other through the network N.

The imaging device 14 is a device that generates a three-dimensional medical image representing a part to be diagnosed of an object to be examined by imaging the part. The three-dimensional medical image captured by the imaging device 14 is formed of a plurality of tomographic images. In the present embodiment, an example in which a computed tomography (CT) device is applied as the imaging device 14 will be described, but the present disclosure is not limited thereto. For example, a device that generates three-dimensional medical images other than a CT device, such as a magnetic resonance imaging (MRI) device or a positron emission tomography (PET) device, may be applied as the imaging device 14. Further, in the present embodiment, an example in which a tomographic image of an axial cross-section is applied as a tomographic image constituting the three-dimensional medical image will be described, but the present disclosure is not limited thereto. A tomographic image of a cross-section other than the axial cross-section, such as a sagittal cross-section and a coronal cross-section, may be applied as the tomographic image constituting the three-dimensional medical image.

The image storage device 16 is a computer that stores and manages medical images, and comprises, for example, a storage device that stores medical images. The image storage device 16 transmits/receives the medical images generated by the imaging device 14 between the contour extraction device 12 and the imaging device 14 through the network N. The storage format of the medical image and the communication between devices through the network N are based on a predetermined protocol, such as digital imaging and communications in medicine (DICOM) or the like.

Next, the hardware configuration of the contour extraction device 12 according to the present embodiment will be described with reference to FIG. 2. Examples of the contour extraction device 12 include a personal computer or a server computer or the like. The contour extraction device 12 may be a cloud server.

Figure 2:
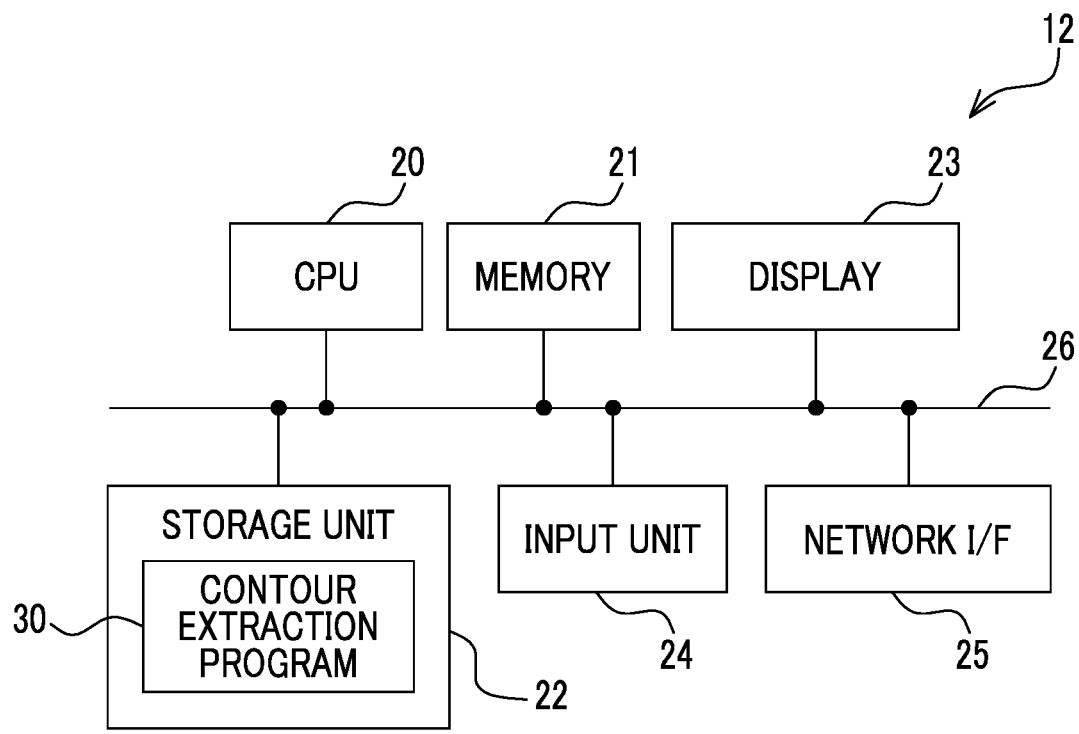
FIG. 2 is a block diagram showing an example of a hardware configuration of a contour extraction device.

As shown in FIG. 2, the contour extraction device 12 includes a central processing unit (CPU) 20, a memory 21 as a temporary storage area, and a nonvolatile storage unit 22. The contour extraction device 12 includes a display 23, such as a liquid crystal display, an input unit 24, such as a keyboard and a mouse, and a network interface (I/F) 25 connected to the network N. The CPU 20, the memory 21, the storage unit 22, the display 23, the input unit 24, and the network I/F 25 are connected to a bus 26.

The storage unit 22 is realized by a hard disk drive (HDD), a solid state drive (SSD), a flash memory, or the like. The storage unit 22 as a storage medium stores a contour extraction program 30. The CPU 20 reads the contour extraction program 30 from the storage unit 22, loads the contour extraction program 30 into the memory 21, and executes the loaded contour extraction program 30.

Figure 3:
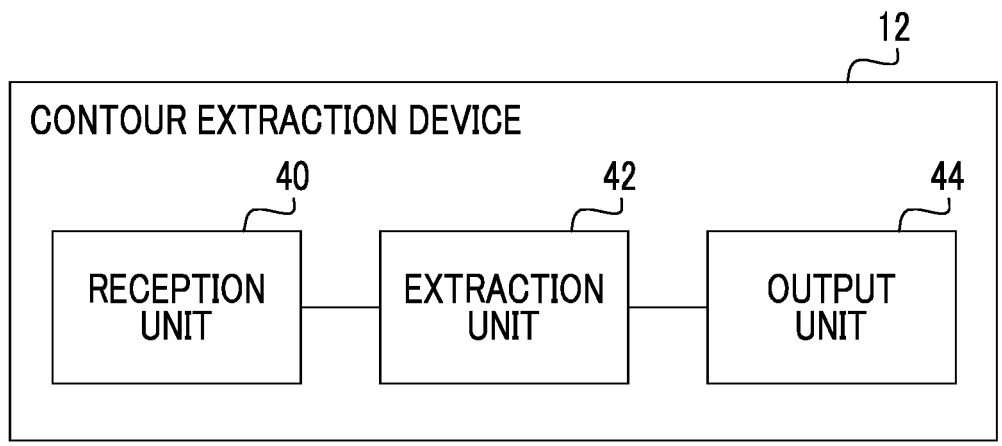
FIG. 3 is a block diagram showing an example of a functional configuration of the contour extraction device.

Next, the functional configuration of the contour extraction device 12 according to the present embodiment will be described with reference to FIG. 3. As shown in FIG. 3, the contour extraction device 12 includes a reception unit 40, an extraction unit 42, and an output unit 44. The CPU 20 executes the contour extraction program 30 to function as the reception unit 40, the extraction unit 42, and the output unit 44.

Figure 4:
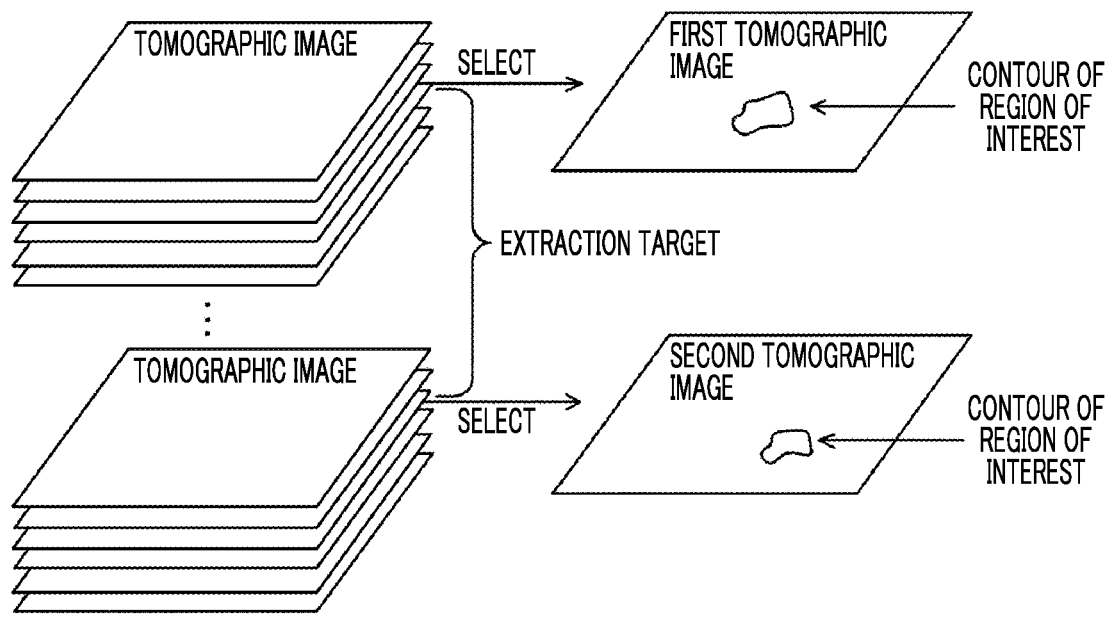
FIG. 4 is a view illustrating contours of regions of interest of first tomographic image and second tomographic image.

As shown in FIG. 4, a user such as a doctor selects, for example, two tomographic images that are tomographic images positionally located at both ends among a tomographic image group, which is an extraction target of a region of interest, from among the plurality of tomographic images, each including the region of interest, the plurality of tomographic images constituting the three-dimensional medical image captured by the imaging device 14. The two selected tomographic images are different tomographic images from each other, and there are a plurality of tomographic images between the two selected tomographic images. The region of interest (ROI) as used herein means a region of interest to the user, for example, a region of a lesion, such as a tumor, and a region of an organ.

Hereinafter, among the two tomographic images selected by the user, one tomographic image is referred to as a "first tomographic image", and the other tomographic image is referred to as a "second tomographic image". Since the accuracy of contour extraction processing of the region of interest, which will be described later, may decrease in a case where the regions of interest included in the first and the second tomographic images are too small, the user selects tomographic images, each of which includes a region of interest having a certain size or larger in the present embodiment.

Next, the user designates a contour of the region of interest of the first tomographic image and a contour of the region of interest of the second tomographic image through the input unit 24. The reception unit 40 receives the contour of the region of interest of the first tomographic image and the contour of the region of interest of the second tomographic image designated by the user. Further, the reception unit 40 receives a contour designated by the user in accordance with a correction instruction output by the output unit 44, which will be described later.

Figure 5:
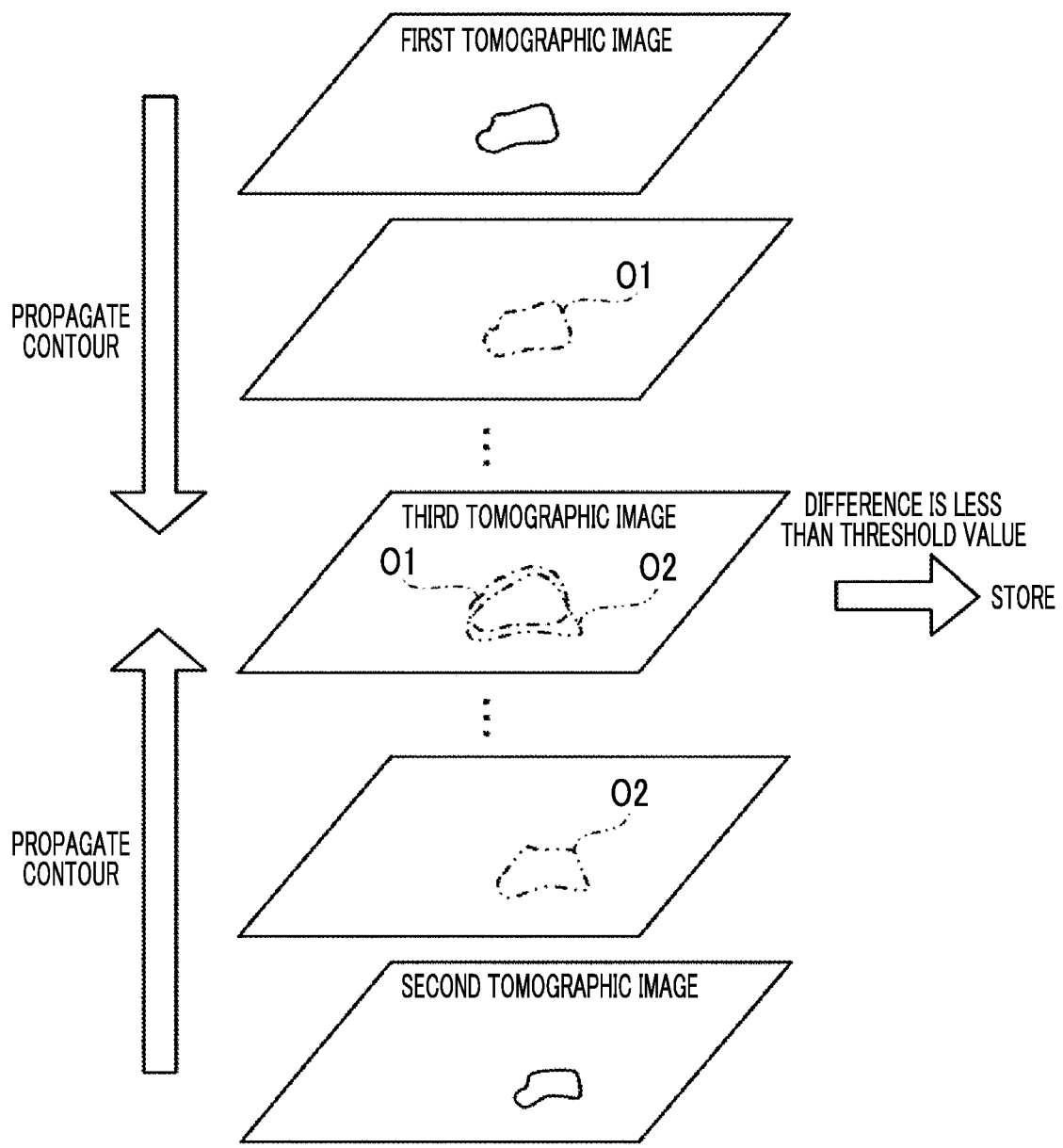
FIG. 5 is a view illustrating contour extraction processing.

The extraction unit 42 propagates the contour of the region of interest of the first tomographic image, which is received by the reception unit 40, in a direction from the first tomographic image to the second tomographic image to extract first contours O1 of the regions of interest of tomographic images between the first and the second tomographic images. In the present embodiment, as shown in FIG. 5, the extraction unit 42 propagates the contour of the region of interest of the first tomographic image from the first tomographic image to a third tomographic image that is a middle tomographic image between the first and the second tomographic images. With this, the extraction unit 42 extracts the first contours O1 of regions of interest of the third tomographic image and of the tomographic image between the first and the third tomographic images. In FIG. 5, the first contour O1 is shown by an alternating long-dash and short-dash line. For example, the extraction unit 42 may extract the first contours O1 from all the tomographic images between the first and the second tomographic images.

Further, the extraction unit 42 propagates the contour of the region of interest of the second tomographic image, which is received by the reception unit 40, in a direction from the second tomographic image to the first tomographic image to extract second contours O2 of the regions of interest of tomographic images between the first and the second tomographic images. In the present embodiment, as shown in FIG. 5, the extraction unit 42 propagates the contour of the region of interest of the second tomographic image from the second to the third tomographic images. With this, the extraction unit 42 extracts the second contours O2 of the regions of interest of the third tomographic image and of the tomographic image between the second and the third tomographic images. In FIG. 5, the second contour O2 is shown by an alternating long-dash and two-short-dash line. For example, the extraction unit 42 may extract the second contours O2 from all the tomographic images between the first and the second tomographic images.

The extraction unit 42 according to the present embodiment uses an active contour method, such as a level set method, for the above-described propagation of the region of interest of the first tomographic image and the above-described propagation of the region of interest of the second tomographic image to extract the first contours O1 and the second contours O2.

As shown in FIG. 5, the output unit 44 outputs the contour of each tomographic image extracted by the extraction unit 42 to the storage unit 22, in a case where the difference between the first contour O1 and the second contour O2, which are extracted by the extraction unit 42, in the third tomographic image is less than a threshold value TH. With this, the contour of each tomographic image is stored in the storage unit 22. The threshold value TH, in this case, is predetermined according to, for example, the required contour extraction accuracy. Further, examples of the difference between the first contour O1 and the second contour O2 include any one of a difference in area, a difference in curvature, or a difference in center of gravity between the first contour O1 and the second contour O2, or a combination of two or more of the above-described examples. The output unit 44 may output the contour of each tomographic image extracted by the extraction unit 42 to the display 23 to make the display 23 display the contour.

On the other hand, the output unit 44 outputs the correction instruction for a contour in the third tomographic image to the display 23 in a case where the difference between the first contour O1 and the second contour O2 in the third tomographic image is the threshold value TH or more. Specifically, in this case, for example, the output unit 44 outputs the third tomographic image and at least one of the first contour O1 or the second contour O2 to the display 23 to make the display 23 display the third tomographic image and the at least one contour. The user corrects the contour of the region of interest on the third tomographic image displayed on the display 23, through the input unit 24. As described above, the contour of the region of interest of this third tomographic image is received by the reception unit 40.

Figure 6:
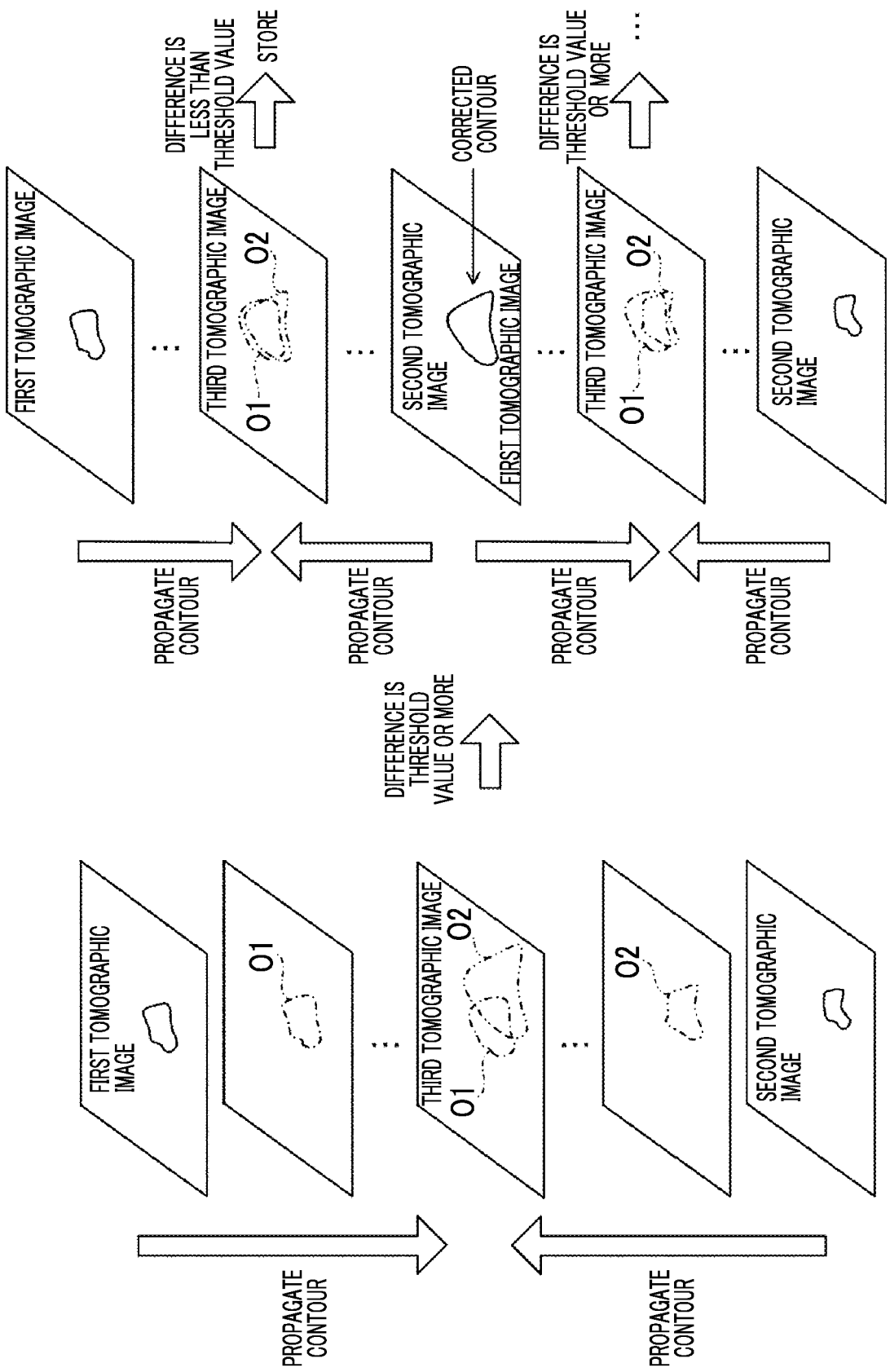
FIG. 6 is a view illustrating the contour extraction processing.

In this case, as shown in FIG. 6, the tomographic image group from the first to the second tomographic images is divided into two tomographic image groups, that is, a first tomographic image group from the first to the third tomographic images and a second tomographic image group from the third to the second tomographic images. Then, the extraction unit 42 performs processing for extracting the first contours O1 and the second contours O2 in the first and the second tomographic image groups in the same manner as in the tomographic image group from the first to the second tomographic images. This processing is repeatedly performed until the difference between the first contour O1 and the second contour O2 in the third tomographic image becomes less than the threshold value TH.

That is, the extraction unit 42 extracts the first contours O1 and the second contours O2 using the contour corrected in accordance with the correction instruction output by the output unit 44 as the contour of the region of interest of the second tomographic image, in the first tomographic image group. Further, the extraction unit 42 extracts the first contours O1 and the second contours O2 using the contour corrected in accordance with the correction instruction output by the output unit 44 as the contour of the region of interest of the first tomographic image, in the second tomographic image group.

Figure 7:
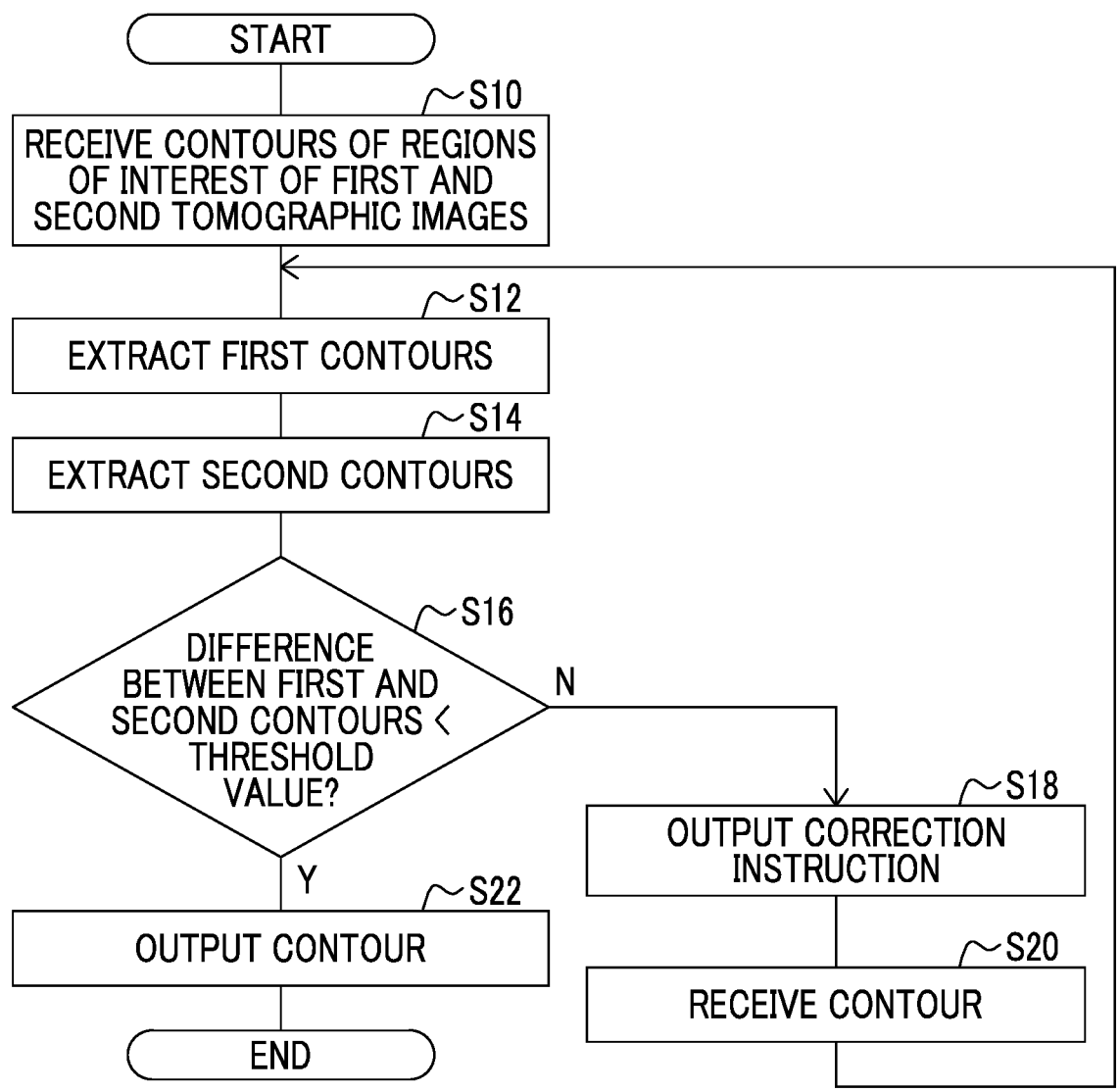
FIG. 7 is a flowchart showing an example of the contour extraction processing.

Next, an operation of the contour extraction device 12 according to the present embodiment will be described with reference to FIG. 7. The CPU 20 executes the contour extraction program 30, whereby the contour extraction processing shown in FIG. 7 is executed. The contour extraction processing is executed, for example, in a case where an execution instruction is input by the user through the input unit 24.

In step S10 of FIG. 7, the reception unit 40 receives the contour of the region of interest of the first tomographic image and the contour of the region of interest of the second tomographic image designated by the user. In step S12, as described above, the extraction unit 42 propagates the contour of the region of interest of the first tomographic image in a direction from the first tomographic image to the second tomographic image to extract the first contours O1 of the regions of interest of the tomographic images between the first and the second tomographic images.

In step S14, as described above, the extraction unit 42 propagates the contour of the region of interest of the second tomographic image in a direction from the second tomographic image to the first tomographic image to extract the second contours O2 of the regions of interest of the tomographic images between the first and the second tomographic images. In step S16, as described above, the output unit 44 determines whether or not the difference between the first contour O1 extracted in step S12 and the second contour O2 extracted in step S14 in the third tomographic image is less than the threshold value TH. In a case where a negative determination is made, the process proceeds to step S18.

In step S18, as described above, the output unit 44 outputs the correction instruction for the contour in the third tomographic image to the display 23. In step S20, the reception unit 40 receives the contour corrected by the user in accordance with the correction instruction output in step S18. When the processing in step S20 ends, the process returns to step S12. In this case, the processing after step S12 is executed using the third tomographic image as the second tomographic image, for the first tomographic image group from the first to the third tomographic images. Further, in this case, the processing after step S12 is executed using the third tomographic image as the first tomographic image, for the second tomographic image group from the third to the second tomographic images.

On the other hand, in a case where an affirmative determination is made in step S16, the process proceeds to step S22. In step S22, the output unit 44 outputs the contour of each tomographic image to the storage unit 22 as described above. When the processing of step S22 ends, the contour extraction processing ends.

As described above, according to the present embodiment, the contour of the region of interest of the first tomographic image is propagated in the direction from the first tomographic image to the second tomographic image, whereby the first contours of the regions of interest of the tomographic images between the first and the second tomographic images are extracted. Further, the contour of the region of interest of the second tomographic image is propagated in the direction from the second tomographic image to the first tomographic image, whereby the second contours of the regions of interest of the tomographic images between the first and the second tomographic images are extracted. Then, the correction instruction for the contour in the third tomographic image between the first and the second tomographic images is output in a case where the difference between the first and the second contours in the third tomographic image is the threshold value or more. Accordingly, the contour of the region of interest can be accurately extracted from the tomographic image.

In the above-described embodiment, the middle tomographic image between the first and the second tomographic images is applied as the third tomographic image, but the present disclosure is not limited thereto. For example, a tomographic image other than the middle tomographic image between the first and the second tomographic images may be applied as the third tomographic image. In this case, for example, a tomographic image having the largest area of the contour extracted by the extraction unit 42 can be applied as the third tomographic image.

Further, in the above-described embodiment, for example, the following various processors can be used as the hardware structures of processing units that execute various kinds of processing, such as the reception unit 40, the extraction unit 42, and the output unit 44. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU, which is a general-purpose processor that executes software (programs) to function as various processing units, as described above.

One processing unit may be constituted of one of the various processors or may be constituted of a combination of two or more processors of the same type or different types (for example, a combination of a plurality of FPGAs and a combination of a CPU and an FPGA). Alternatively, the plurality of processing units may be constituted of one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and a server. A second example of the configuration is an aspect in which a processor that implements all of the functions of a system including the plurality of processing units with one integrated circuit (IC) chip is used. A representative example of the aspect is a system on chip (SoC). As described above, various processing units are constituted of one or more of the various processors as the hardware structures.

Furthermore, as the hardware structures of the various processors, more specifically, an electrical circuit (circuitry) in which circuit elements, such as semiconductor elements, are combined can be used.

In the above-described embodiment, the aspect in which the contour extraction program 30 is stored (installed) in the storage unit 22 in advance has been described, but the present disclosure is not limited thereto. The contour extraction program 30 may be provided in a form in which the contour extraction program 30 is recorded on a recording medium, such as a compact disc read only memory (CD-ROM), a digital versatile disc read only memory (DVD-ROM), and a Universal Serial Bus (USB) memory. Alternatively, the contour extraction program 30 may also be provided in a form in which the contour extraction program 30 is downloaded from an external device through the network.

EXPLANATION OF REFERENCES

10: diagnosis support system
12: contour extraction device
14: imaging device
16: image storage device
20: CPU
21: memory
22: storage unit
23: display
24: input unit
25: network I/F
26: bus
30: contour extraction program
40: reception unit
42: extraction unit
44: output unit
N: network
O1, O2: contour

What is claimed is:
1. A contour extraction device comprising:
at least one processor,
wherein the processor
propagates a contour of a region of interest of a first tomographic image in a three-dimensional image, which is formed of a plurality of tomographic images, each including the region of interest, in a first direction from the first tomographic image to a second tomographic image to extract first contours of the regions of interest of tomographic images between the first tomographic image and the second tomographic image, and
propagates a contour of the region of interest of the second tomographic image in a second direction from the second tomographic image to the first tomographic image to extract second contours of the regions of interest of tomographic images between the first tomographic image and the second tomographic image, wherein the first direction is opposite to the second direction, and outputs a correction instruction for a contour in a third tomographic image between the first tomographic image and the second tomographic image in a case where a difference between the first contours and the second contours in the third tomographic image is a threshold value or more, wherein the processor, in a case where the difference is the threshold value or more, extracts the first contours and the second contours using a contour corrected in accordance with the correction instruction as the contour of the region of interest of the second tomographic image, in a tomographic image group from the first tomographic image to the third tomographic image.

2. The contour extraction device according to claim 1, wherein the processor outputs the extracted contour of each tomographic image in a case where the difference is less than the threshold value.

3. The contour extraction device according to claim 1, wherein the third tomographic image is a middle tomographic image between the first tomographic image and the second tomographic image in the plurality of tomographic images.

4. The contour extraction device according to claim 1, wherein the processor extracts the first contours and the second contours using an active contour method.

5. A contour extraction method that is executed by a processor provided in a contour extraction device, the method comprising:

propagating a contour of a region of interest of a first tomographic image in a three-dimensional image, which is formed of a plurality of tomographic images, each including the region of interest, in a first direction from the first tomographic image to a second tomographic image to extract first contours of the regions of interest of tomographic images between the first tomographic image and the second tomographic image, and propagating a contour of the region of interest of the second tomographic image in a second direction from the second tomographic image to the first tomographic image to extract second contours of the regions of interest of tomographic images between the first tomographic image and the second tomographic image, wherein the first direction is opposite to the second direction; and outputting a correction instruction for a contour in a third tomographic image between the first tomographic image and the second tomographic image in a case where a difference between the first contours and the second contours in the third tomographic image is a threshold value or more, in a case where the difference is the threshold value or more, extracting the first contours and the second contours using a contour corrected in accordance with the correction instruction as the contour of the region of interest of the second tomographic image, in a tomographic image group from the first tomographic image to the third tomographic image.

6. A non-transitory computer readable recording medium storing a contour extraction program for causing a processor provided in a contour extraction device to execute a process comprising:

propagating a contour of a region of interest of a first tomographic image in a three-dimensional image, which is formed of a plurality of tomographic images, each including the region of interest, in a first direction from the first tomographic image to a second tomographic image to extract first contours of the regions of interest of tomographic images between the first tomographic image and the second tomographic image, and propagating a contour of the region of interest of the second tomographic image in a second direction from the second tomographic image to the first tomographic image to extract second contours of the regions of interest of tomographic images between the first tomographic image and the second tomographic image, wherein the first direction is opposite to the second direction; and outputting a correction instruction for a contour in a third tomographic image between the first tomographic image and the second tomographic image in a case where a difference between the first contours and the second contours in the third tomographic image is a threshold value or more, in a case where the difference is the threshold value or more, extracting the first contours and the second contours using a contour corrected in accordance with the correction instruction as the contour of the region of interest of the second tomographic image, in a tomographic image group from the first tomographic image to the third tomographic image.

7. The contour extraction device according to claim 1, wherein the processor extracts the first contours and the second contours using the contour corrected in accordance with the correction instruction as the contour of the region of interest of the first tomographic image, in a tomographic image group from the third tomographic image to the second tomographic image.

* * * * *